United States Patent [19]

Short et al.

[11] 4,221,731
[45] Sep. 9, 1980

[54] PROCESS FOR RECOVERY OF HIGH-GRADE LECITHIN AND SOLVENTS FROM TERNARY SOLVENT SYSTEM CONTAINING CRUDE VEGETABLE OIL

[75] Inventors: Robert G. Short; Frank T. Orthoefer, both of Decatur, Ill.

[73] Assignee: A. E. Staley Manufacturing Company, Decatur, Ill.

[21] Appl. No.: 897,969

[22] Filed: Apr. 19, 1978

[51] Int. Cl.$^2$ ............... A23J 7/00; C07F 9/02; C11C 3/00
[52] U.S. Cl. ............... 260/403; 260/412.4; 260/412.8; 260/123.5
[58] Field of Search ............... 260/403, 412.4, 123.5

[56] References Cited

U.S. PATENT DOCUMENTS

| | | | |
|---|---|---|---|
| 2,615,905 | 10/1952 | Heinrich | 260/403 |
| 3,357,918 | 12/1967 | Davis | 426/662 |
| 3,714,210 | 1/1973 | Schweiger | 260/123.5 |
| 3,878,232 | 4/1975 | Hayes | 260/403 |
| 3,998,800 | 12/1976 | Youngquist | 260/123.5 |

*Primary Examiner*—John F. Niebling
*Attorney, Agent, or Firm*—M. Paul Hendrickson; Charles J. Meyerson

[57] ABSTRACT

A method of recovering a high-grade lecithin and solvents from an oil-bearing full miscella which also contains lecithin and which results from an oilseed ternary solvent extraction process. The method may include a first step of phase separation of the oil-bearing miscella containing lecithin and the ternary solvents into a polar and a non-polar phase, and a second step of azeotropic distillation of the non-polar phase to recover a portion of the solvents, and to remove substantially all the water from the residual crude oil, thereby keeping the lecithin in solution. A commercial grade lecithin having good water dispersibility is subsequently recovered from the residual crude oil, and a small amount of highly water dispersible lecithin may be recovered from the polar phase by atmospheric distillation.

In another embodiment, when the full miscella containing crude oil ternary solvent and lecithin resulting from the above ternary solvent extraction is initially subjected to azeotropic distillation to recover solvent therefrom and remove substantially all the water, a highly water dispersible lecithin having a high choline chloride content is obtained. Premature degumming of this highly water dispersible lecithin is avoided by maintaining the solvent ratios above certain minimums.

The ternary solvents for the oilseed extraction include a lipophilic hydrocarbon, such as hexane; a water miscible lower alcohol, such as ethanol; and a minor amount of water. The recovery method is energy efficient, because the boiling temperature of the ternary azeotrope is lower than any other combination of the three solvents.

20 Claims, No Drawings

PROCESS FOR RECOVERY OF HIGH-GRADE LECITHIN AND SOLVENTS FROM TERNARY SOLVENT SYSTEM CONTAINING CRUDE VEGETABLE OIL

BACKGROUND

In the solvent extraction of oil seed materials, such as soybean, cottonseed, sunflower seed, rapeseed, peanut and the like with a ternary solvent system such as hexane/alcohol and water, one of the difficulties encountered has been solvent recovery from the oil-bearing miscella. In the past, when insufficient hydrocarbon solvent was used, an oil residue containing excess water caused the phosphatides (lecithin) to become viscous, and to precipitate out of the liquid phase prematurely, thereby causing probems in the liquid lines of the process system.

PRIOR ART

U.S. Pat. No. 3,878,232, issued to a common assignee herewith, discloses the general concept of phase separation in a ternary solvent system. In that patent, it is stated that, in order to effectively separate and remove high-grade lecithin from a mixed aqueous/lipid miscella obtained from solvent extraction of soybean flakes, it is essential that the monohydric alcohol in the system be greater than 40% and less than 70% of the admixed miscella polar phase weight. The admixture is then separated into a polar phase and a non-polar phase. The patent states that the non-polar phase consists essentially of a high-lecithin-containing oil and hexane, and the resulting aqueous or polar phase contains substantially all of the soybean liquid extracts which are soluble in the polar phase water/monohydric alcohol solvent system. The polar and non-polar phases are separated by conventional means. See Column 7, lines 16–67, of U.S. Pat. No. 3,878,232.

The subject U.S. Pat. No. 3,878,232 did not combine the particular solvent ratios which are important to the success of the process of the subject invention, and with a preliminary phase separation step to take full advantage of both the energy efficient azeotropic distillation principle and the phase separation principle. Applicants' process utilizes the advantage of phase separation as a means of adjusting the solvent composition to minimize energy requirements by utilizing azeotropic distillation in solvent recovery. Prior to phase separation solvent ratios are adjusted as necessary to insure that all water will be removed from the lecithin-containing crude oil residue during distillation to insure that the lecithin remains suspended in the oil phase until a later step in the process.

The three component solvent composition is carefully monitored in the subject process to insure that the ratio of hydrocarbon to alcohol, and of alcohol to water, are maintained above certain levels to insure that all water will be removed from the non-polar crude oil residue after phase separation and azeotropic distillation.

U.S. Pat. No. 3,998,800 is directed to a method of solvent extracting oilseeds, such as soybean, using a ternary, single-phase solvent comprising 30–90 wt. % non-polar hydrocarbon (hexane); 10–69.9 wt. % alcohol (ethanol); and 0.1–10 wt. % water. This patent states that it is critical to maintain a single-phase ternary solvent, and that it is important to keep the water content below 10 wt. %. The extraction temperature disclosed is from about 30° C. up to about the boiling point of the system, which is disclosed to be 56° C. Example I of U.S. Pat. No. 3,998,800 states that the hexane/ethanol/water system described can be recycled with maintenance of constant composition with relatively simple distillation equipment. It is stated that the particular mixture of the three components single-phase solvent system is an azeotrope boiling at 58.7° C. It is further observed that the total hexane/ethanol/water system exhibits an azeotrope at 56° C. in the gas phase, which separates into two phases upon condensing. The upper phase containing 96.5 wt. % hexane; 3.0 wt. % ethanol; and 0.5 wt. % water. The lower phase contains 75 wt. % hexane; 6 wt. % ethanol; and 19 wt. % water. Although this patent recognizes the existence of an azeotrope of hexane/ethanol/water which boils at 56° C., and that it does split into two phases, the patent does not take advantage of the combined steps of phase separation and azeotrope distillation to recover solvent in a manner which is energy efficient, and by which an improved lecithin product is recovered from the non-polar phase of the system.

Various proposals have been made to produce a more desirable lecithin from oilseed processing. A more fluid lecithin is desirable from the point of view of easy handling and dispersing. U.S. Pat. No. 3,357,918 summarizes some of the methods used to fluidize lecithin, and that patent is directed to the addition of divalent metal salts to lecithin to obtain a more fluid product. The process uses cations of calcium, magnesium and aluminum, and anions of chloride, acetate, and nitrate to obtain a fluid product. In contrast, applicants' method produces a good quality lecithin without the addition of divalent metal cations.

U.S. Pat. No. 3,962,292 describes another process for modifying a natural phosphatide to develop water dispersibility. This latter method includes steps of acylation, hydroxylation and neutralization. A combination of acylation and hydroxylation of the phosphatide (lecithin) was said to give significantly improved water dispersibility. Again, the improvement is obtained by an added process step which involves extra expense.

U.S. Pat. No. 2,615,905 discloses simultaneously debittering and deoiling the seeds of bitter lupine (an oilseed grown in Europe). For this purpose, a ternary azeotropic solvent comprising water, a water-miscible polar organic solvent (ethanol) and a lipophilic organic solvent (benzene, petroleum ether, carbon tetrachloride, trichloroethylene, chloroform and the like) is used. The preferred lipophilic solvent is benzene. The boiling point of the azeotrope is 64.9° C. when it comprises about 74% benzene, 18.3% ethanol, and 7.7% water. The *preferred* solvent contains a little more ethanol to *avoid* separating into two layers at lower temperatures. See U.S. Pat. No. 2,615,905, Column 4, lines 22–51. Although this patent does state that the water level in the solvent-water mixture should not exceed the water content of the ternary azeotropic mixture, it does not specify a ratio of lipophilic solvent to water miscible polar solvent, nor does it disclose an initial step of phase separation to facilitate azeotropic distillation.

Other solvent extraction systems have been described for processing soybeans to obtain lecithin. For example, U.S. Pat. No. 3,268,335 describes hexane extraction of soy flakes to obtain solvent saturated non-degummed soy oil. The hexane solvent is distilled off, and the oil is subjected to a water/centrifuge treatment. A degummed oil and a lecithin emulsion are obtained. The lecithin emulsion is dried and then treated with acetone to produce oil and soy phosphatide. The phosphatide is subjected to alcohol treatment to produce alcohol soluble, and alcohol insoluble, phosphatides. In contrast, the solvent treatment process of the subject invention recovers substantially all of a highly water dispersible lecithin in the oil phase.

GENERAL DESCRIPTION

This invention comprises an improved method of handling ternary solvents in processes using such solvents for oil extraction from oilseed. It is expected that the advantages of the method will accrue in most oilseed ternary solvent extraction processes, but in particular, it is applicable to ternary solvent extraction processes in which water is present in the oil-bearing miscella extracted from the oilseed, and in which the oil-bearing miscella includes a water-dispersible, gum-like substance such as phosphatide (lecithin). Such substances tend to hydrate from the desolventized or partially desolventized oil-bearing miscella in the presence of water.

The present method removes substantially all water from the oil-bearing miscella by azeotropic distillation of the ternary solvents therefrom, taking care that the solvents are present in the oil-bearing miscella at ratios to insure substantially complete removal of water by a means of azeotropic distillation. The ratios can be adjusted by simply adding any one or more of the solvents, or by careful phase separation prior to distillation, or by a combination of both procedures. In situations where an oil-bearing miscella from a second oilseed extraction process using one or more of the solvents is available, such miscella may be mixed with a water-containing miscella to adjust the solvent ratios, with or without phase separation, to those values which will remove substantially all water from the mixed miscella by azeotropic distillation.

Oilseeds which may be subjected to solvent extraction to obtain oil-bearing miscella which may be further treated using the subject method include soybean, cottonseed, sunflower, safflower, flax (linseed), sesame, lupine, maize, rapeseed, peanut, coconut, field pea and horse bean. The detailed description below shows application of the method to soybean.

The solvent system includes a lipophilic solvent and an organic solvent which is miscible in the lipophilic solvent and in water. The water may be introduced into the system intentionally, or as moisture either in the oilseed, or otherwise. Typical lipophilic solvents include: alkanes, such as hexane; substituted alkanes, such as dichlorodifluoromethane; possibly other hydrocarbons, including alkenes such as benzene. Hexane is preferred. Possible water miscible solvents include: lower alkanols, such as butanol, isopropyl alcohol, ethanol and methanol; ketones, including acetone; and substituted alkanols. Ethanol is preferred.

The main advantage of the subject process is improved handling of oil-bearing miscella containing solvents including water and also including hydratable materials which tend to degum after the solvents are partially removed without also removing substantially all of the water. The subject process accomplishes removal of substantially all the water by steps including adjustment of the solvent ratios in the oil-bearing miscella, phase separation and azeotropic distillation of substantially all water from the oil-bearing miscella containing the hydratable materials. A hydratable material having improved water-dispersibility also is obtained from the subject process.

DETAILED DESCRIPTION

A general outline of the subject process is set forth below:

STARTING COMPOSITION
Phase Separation of Full Miscella and Theoretical Desolventizing

|  |  | Oil | Hexane | Alcohol | Water |
|---|---|---|---|---|---|
| 888.89 | Full Miscella | 121.07 | 694.04 | 70.67 | 3.11 |
| 88.89 | 95% Alcohol |  |  | 84.44 | 4.44 |
| 22.22 | Water |  |  |  | 22.22 |
| 1000.00 | Total Parts* | 121.07 | 694.04 | 155.11 | 29.77 |

849.60 Upper Phase
14.07% Oil = 119.54
80.34% Hexane = 682.57
5.33% Alcohol = 45.28
0.26% Water = 2.21

150.40 Lower Phase
1.02% Oil = 1.53
7.62% Hexane = 11.47
73.02% Alcohol = 109.83
18.33% Water = 27.57

B.P. 56° C.

→ 73.67 Ternary Solvent
85% Hexane = 62.62
12% Alcohol = 8.84
3% Water = 2.21

→ 13.49 Ternary Solvent
85% Hexane = 11.47
12% Alcohol = 1.62
3% Water = 0.40

119.54 Oil
619.95 Hexane
36.44 Alcohol
775.93

1.53 Oil
108.21 Alcohol
27.16 Water
136.90

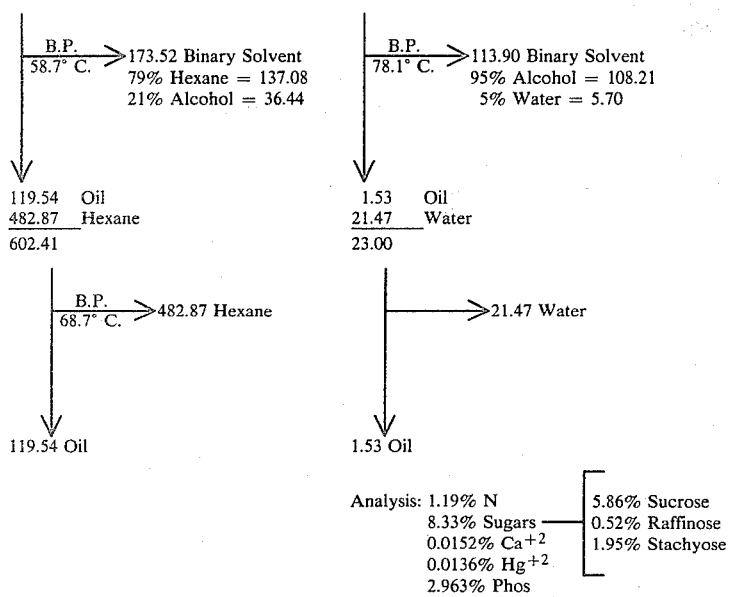

*Unless otherwise specified, all amounts are in parts.

In the above outline, the 888.89 parts full miscella comprised 121.07 parts oil; 694.04 parts hexane; 70.67 parts alcohol; and 3.11 parts water. These relative amounts provide hexane/alcohol ratio of 9.82 and an alcohol/water ratio of 22.72, which is far in excess of the minimum ratios of 7.1 hexane/alcohol and 4.0 alcohol/water required to obtain complete azeotropic distillation removal of all water from the system.

However, the above solvent proportions produce a single phase system, so alcohol and water are added as indicated to force a phase separation, but to still keep the solvent ratios in the non-polar phase above those required to allow ternary solvent azeotropic distillation of the resulting polar phase and complete removal of the water from the oil residue remaining after the ternary solvent azeotropic distillation has been completed.

After the additions of 88.89 parts of 95% alcohol, and 22.22 parts water, it can be seen that the initial proportions of hexane/alcohol and water in the starting compositions are such that the hexane content total is less than 7.1 times the alcohol. The alcohol content, however, is more than 4 times the water content in the overall system. These proportions are sufficient to force a phase separation.

The ratio of hexane to alcohol in the single phase full miscella is more than 7.1:1 and the ratio of alcohol to water in the full miscella is much more than 4:1, and this single phase system is not easily separated, although the full miscella can be subjected to azeotropic distillation since the solvent ratios are high enough. This possible embodiment of the method and results obtained will be discussed later.

In the embodiment, outlined above, it is most important to obtain a good "partition" effect in the phase separation so that substantially all the undesirable components go with the lower, polar phase. For this reason, additional alcohol and water are added to the full miscella so that *after* the phase separation, the ratios of hexane/alcohol and alcohol/water exceed 7.1 and 4, respectively, in the non-polar upper phase to facilitate azeotropic distillation of the solvents and substantially complete removal of water from the lecithin-containing crude oil residue. It can be seen that the hexane/alcohol ratio is 15.07:1, and the water/alcohol ratio is 20.49:1 in the upper phase after phase separation as set forth in the outline.

This upper phase containing ternary solvents, crude soybean oil and lecithin is subjected to distillation in a rising film evaporator, or other suitable equipment capable of heating the liquid mixture to vaporize the solvent mixture. It is at this point that the maintenance of the minimum ratios of hexane/alcohol and alcohol/water is important. Because there is sufficient hexane and alcohol in the system, and not an excess of either alcohol or water, all of the water is carried over into the distillate condensate, and is collected for recovery and later reuse. It is important to remove all water from the crude soybean oil at this point because the presence of water causes premature degumming of the phosphatides (lecithin) in the crude oil residue from the distillation step.

There is another important advantage to having the ratios as specified. The distillation is accomplished at the lowest possible temperature (56° C.), which is the azeotrope boiling point for hexane/alcohol/water at atmospheric pressure. When all of the water has been removed from the liquid, the vaporization temperature of the remaining hexane/alcohol mixture thereupon changes to 58.7° C., and this binary solvent mixture is removed at the ratio of 79% hexane/21% alcohol, leaving only hexane and lecithin-containing soybean oil behind, but in a stable solution which does not prematurely "degum."

The lecithin-containing oil/hexane liquid mixture then enters a falling film evaporator which has a vacuum system. Substantially all but traces of the hexane is removed at the vaporization temperature of about 50°–55° C., and an absolute pressure of about 14.5–20 inches Hg in the falling film evaporator.

The lecithin-containing crude oil is then subjected to "steam" stripping to remove the last traces of hexane. Trace amounts of hot water are sprayed into the oil in a direction countercurrent to the oil. This action removes the remaining trace amounts of hexane, and the small amount of water used evaporates, leaving only the lecithin-containing oil.

The lecithin-containing crude soybean oil is then sent to the oil refinery for further processing which includes degumming. In this step, the lecithin (phosphatides) is separated from the oil.

Degumming of the oil to remove lecithin (phosphatides) may be accomplished by different methods. The following method is typical. The crude oil is heated to about 160° F. (71.1° C.) and acetic anhydride is added, followed by the addition of water to form a lecithin (phosphatide) hydrate/oil admixture. This admixture is then subjected to a separation technique, such as centrifuging. The degummed oil is centrifugally separated from the hydrated lecithin and is sent to additional processing and other final refining steps.

The hydrated lecithin phosphatide which has been centrifugally separated is then dried. The composition of the dried lecithin is approximately:

| Tocopherol (ppm) | Choline Chloride (ppm) | Sterols %: Total: | Campesterol (%) | Stigmasterol (%) | Sitosterol (%) |
|---|---|---|---|---|---|
| 282 | 628 | 0.72 | 0.16 | 0.17 | 0.39 |

The above lecithin has good dispersibility, and can be combined with lecithins obtained from conventional hexane extracted soybean oils with no adverse effect.

In another embodiment of the process outlined above, the full miscella is subjected to azeotropic distillation without first subjecting the full miscella to phase separation, but with solvent ratio adjustment as required. Surprisingly, a highly water dispersible lecithin can then be obtained from the crude oil. The method of separation of this lecithin generally follows the above described process, but without the phase separation step. The highly water dispersible lecithin obtained has the following approximate analysis:

| Tocopherol (ppm) | Choline Chloride (ppm) | Sterols %: Total: | Campesterol (%) | Stigmasterol (%) | Sitosterol (%) |
|---|---|---|---|---|---|
| 363 | 1800 | 0.54 | 0.13 | 0.13 | 0.28 |

The surprisingly high level of choline chloride and significantly higher level of tocopherol are the main differences of this highly water dispersible lecithin from water dispersible lecithin described below. It is presently believed that the additional choline chloride accompanies the alcohol solvent when phase separation is used in the above process. It is also believed that the much larger proportion of choline chloride in the lecithin obtained from direct azeotropic distillation without the prior phase separation contributes to its substantially greater water dispersibility.

In the embodiment of the invention shown in the above outline, the major part of the alcohol goes into the lower, polar phase, and it is believed that the major proportion of choline chloride which has been solvent extracted is carried over into this lower, polar phase. The further processing of this lower, polar phase is described later herein.

The highly water dispersible lecithin obtained from the process described immediately above (without phase separation) is useful in blends with lecithins of less water dispersibility, which otherwise ordinarily require alkali modification or some other modification to make such lecithins water dispersible. It has been discovered that blending about 10%–30% by weight of the subject water dispersible lecithin with 90–70% untreated lecithin obtained from hexane extracted oil results in a blended lecithin product having good water dispersibility.

Emulsification tests were conducted to compare the subject blended lecithin with a standard lecithin, and with an alkali modified lecithin. The blended lecithin product was nearly equivalent to the alkali modified lecithin (obtained from hexane extracted oil, and then treated further with alkali). When the blended lecithin product was subjected to the alkali modification, it lost emulsification stability, so it is clear that not only does the blended product not require the alkali modification, such treatment is actually detrimental to its emulsification properties.

Returning to the process outline, it should be noted that the lower, polar phase resulting from the phase separation contains very little oil, a relatively large amount of alcohol, a somewhat lesser amount of water, and an even less amount of hexane. The hexane/alcohol ratio is about 0.1:1 and the alcohol/water ratio is about 3.8:1. About 10% of this solvent mixture is capable of azeotropic distillation at 56° C. at atmospheric pressure to remove the hexane and recover it for reuse in the extraction system. The residue from this distillation step contains a major proportion of alcohol (108.21 parts); a lesser amount of water (27.16 parts); and a minor amount of oil (1.53 parts).

The alcohol/water solvent containing the minor amount of oil residue is subjected to distillation and it vaporizes off at 78° C. as 95% alcohol/5% water, leaving only the minor oil residue and 21.47 parts water. The water can then be separated from this oil by conventional means, such as phase separation. This residual crude oil has the analysis set forth in the outline. This minor crude oil residue is then sent to the animal feed preparation system where it is combined with other condensed soy soluble residues. Since the residues contain a relatively large percentage of sugars (sucrose, raffinose and stachyose) it has been found that the condensed soy solubles make an excellent replacement for sugar cane molasses binders in animal feeds, including animal feed blocks. The resulting blocks have better weathering properties. This improved animal feed block is covered by a separate patent application by others, and is not part of the subject invention.

The following specific examples illustrate the importance of the combined steps of the subject invention to obtain all the advantages in the improved overall process, including energy conservation, improved phase separation and by-product separation, improved handling and an improved water-dispersible lecithin by-product.

The advantages obtained when an oil miscella having the proper hexane/alcohol and alcohol/water ratios of at least 7.1:1 and 4:1, respectively are illustrated by the following example:

EXAMPLE 1

An oil miscella having the following composition was desolventized without prior phase separation at atmospheric pressure:

| Oil Miscella Composition | Solvent Ratios |
|---|---|
| 11.29% oil | hexane/alcohol 7.2:1 |
| 1.11% water | |
| 10.67% alcohol | alcohol/water 9.6:1 |
| 76.93% hexane | |

The desolventizing was performed at 56° C. (the vaporization temperature of the ternary azeotrope of hexane/alcohol/water). The desolventizing was stopped when the temperature changed. The single phase residue was 33.33% of the total weight of the oil miscella prior to desolventizing, and contained only oil and hexane by analysis. The ternary solvent which was vaporized and then condensed 85% hexane/12% alcohol and 3% water. All of the water, but only a very minute amount of entrained oil were removed from the desolventized residue. The ternary azeotrope obtained by desolventizing the above oil miscella contained 31.45 parts hexane (85 wt. %); 4.44 parts alcohol (12 wt. %); and 1.11 parts water (3 wt. %). The boiling temperature of the mixture then changed to 58.7° C., the vaporization temperature of the binary azeotrope of hexane/alcohol, and 23.44 parts hexane (79 wt. %); and 6.23 parts alcohol (21 wt. %) came off remainder comprising 22.04 parts hexane (66.13 wt. %) and 11.29 parts lecithin-containing crude oil (33.87 wt. %). The hexane was then vaporized off at 68.7° C., leaving the lecithin-containing crude oil.

EXAMPLE 2

When an oil miscella having a hexane/alcohol ratio lower than 7.1:1 is desolventized without prior phase separation even though the alcohol/water ratio is at least 4:1, the results are less desirable, as illustrated below:

| Oil Miscella Composition | Solvent Ratios |
|---|---|
| 8.99% oil | hexane/alcohol 1.58:1 |
| 7.13% water | |
| 32.51% alcohol | alcohol/water 4.56:1 |
| 51.37% hexane | |

Partial desolventizing was performed at atmospheric pressure and a temperature of 56° C. as before until the temperature changed. At this point, 54.7% of the oil miscella remained, only 45.3% having been removed by azeotropic distillation. The residue comprised three phases (two layered phases with drops of a third phase in each layer) and it had the following composition:

| Oil Solvent Residue Composition |
|---|
| 19.85% oil |
| 12.12% water |
| 57.28% alcohol |
| 10.76% hexane |

The presence of water in the oil residue is undesirable, and creates an unwanted three phase condition, which makes more difficult the further separation of the solvents from the crude oil. The drops in each layer phase of the system are believed to comprise water, and the improper solvent ratios have unnecessarily complicated the further separation of the solvents from the lecithin-containing crude soybean oil.

EXAMPLE 3

When the alcohol/water ratio is below 4:1, even though the hexane/alcohol ratio is above 7.1:1 there is a serious premature degumming problem, as illustrated below:

| Oil Miscella Composition | Solvent Ratios |
|---|---|
| 11.00% oil | hexane/alcohol 7.21:1 |
| 2.99% water | |
| 10.48% alcohol | alcohol/water 3.52:1 |
| 75.47% hexane | |

Partial desolventizing as described above in Examples 1 and 2 was performed. Although, 86.2% of the oil miscella was removed by azeotropic distillation at a temperature of 56° C., the residue contained an excess of water and the oil degummed prematurely. This creates serious oil handling problems and fouls the desolventizing lines.

EXAMPLE 4

This example illustrates the substantial advantages of oil recovery, solvent recovery and lecithin recovery which are obtained by initial phase separation of the oil miscella which does not have the minimum required solvent ratios in combination with observing the required solvent ratios in the non-polar phase prior to desolventizing.

| Oil Miscella Composition | Initial Solvent Ratios |
|---|---|
| 19.13% oil | hexane/alcohol 3.37:1 |
| 1.88% water | |
| 18.08% alcohol | alcohol/water 9.62:1 |
| 60.91% hexane | |

The above miscella will not desolventize properly at the above solvent ratios, as illustrated by Example 2. The above oil miscella was first phase separated to yield the following phases:

| 84.35% non-polar phase | 15.65% polar phase |
|---|---|
| 22.19% oil | 2.64% oil |
| 1.01% water | 6.57% water |
| 8.09% alcohol | 71.92% alcohol |
| 68.71% hexane | 18.87% hexane |

The above non-polar phase contains 97.86% or almost 98% of the oil, and it has a hexane/alcohol ratio of 8.02 and an alcohol/water ratio of 8.50, both well above the minimum ratios required to successfully desolventize the oil as described in Example 1 above. The polar phase is, of course, treated in the conventional manner as set forth above in the process outline.

SUMMARY

By virtue of the simple, energy efficient phase separation, the advantages of lower energy azeotropic distillation can be realized to further separate the crude oil from the ternary extraction solvents. Because of the total water removal made possible by observing the minimum solvent ratios, the phosphatide (lecithin) contained in the crude oil does not degum prematurely. An improved water dispersible lecithin having increased water dispersibility is thereafter obtained from the oil at the regular degumming station in the process.

Phase separation may be first employed on the full miscella containing the crude oil, lecithin and the ternary solvents to insure that the ratios of hydrocarbon to alcohol, and lower alcohol to water, are maintained above a certain minimum to assure that all water is removed from the crude oil residue during azeotropic distillation recovery of the solvents. Removal of the water avoids premature degumming of the lecithin from the crude oil residue.

In another embodiment, the full oil miscella resulting from the ternary solvent extraction process is subjected to azeotropic distillation desolventizing without first subjecting it to phase separation. The solvent ratios are first adjusted as necessary prior to such desolventizing to insure removal of all water from the solvent. When this latter procedure is followed, a highly water dispersible lecithin having an unusually high choline chloride content is obtained. This highly water dispersible lecithin can be blended with hydrocarbon solvent extracted lecithin of lower water dispersibility to improve the overall water dispersibility of the blended lecithin.

The subject water dispersible lecithins obtained by the process of the invention can be used in foods and many industrial applications. It is an excellent emulsifying agent, and has good wetting properties. Lecithin is also used in liquid animal feeds, for example, soybean lecithin is used in substitute liquid feeds for calves so that the cow's milk can be sold as human food.

We claim:

1. In a solvent extraction method of extracting oil from oilseed using a ternary solvent mixture including a oleophilic hydrocarbon solvent; a lower alcohol solvent which is miscible with water and with said hydrocarbon solvent; and water; and one of the extracted materials is a full miscella containing crude oil, phosphatides and said ternary solvent mixture, the steps of:
   a. separating the full miscella into an upper and lower phase, said upper phase containing: crude oil, phosphatides, hydrocarbon solvent, lower alcohol solvent, and water in which the ratio of hydrocarbon solvent to lower alcohol and lower alcohol to water both exceed the ratios of the respective solvents in the ternary azeotrope formed by said solvents with water when heated to the ternary azeotropic vapor temperature; and
   b. thereafter subjecting said upper phase to heat to cause the ternary solvent mixture to vaporize at its azeotropic distillation temperature to thereby remove substantially all water from said upper phase, leaving only crude oil, phosphatides, hydrocarbon solvent, and lower alcohol solvent, whereby premature degumming of said phosphatides is avoided by first removing all water from said upper phase.

2. The method of claim 1, in which the oilseed is soybean and the ternary solvents comprise hexane, a lower alcohol, and water.

3. The method of claim 2, in which the lower alcohol is ethanol.

4. The method of claim 3, in which the solvent ratios after phase separation exceeds 7.1 parts hexane:1 part ethanol; and 4.0 parts ethanol:1 part water.

5. The method of claim 4, in which the azeotropic distillation temperature of said ternary solvent mixture is about 56° C. at atmospheric pressure, and including the step of continuing the distillation until the temperature of the vapor phase changes from 56° C., thereby insuring complete removal of water from said upper phase, leaving a binary solvent mixture of hexane and ethanol.

6. The method of claim 5, including the step of continuing the distillation at about 58.7° C., the vaporization temperature of the binary solvent mixture of hexane and ethanol, until the temperature of the vapor phase again changes, thereby insuring complete removal of ethanol from said non-aqueous liquid phase leaving only hexane solvent, crude oil and phosphatides.

7. The method of claim 6, including the step of continuing the distillation at a temperature of about 68.7° C., the vaporization temperature of hexane, until the temperature again changes to insure substantially complete removal of hexane from said non-aqueous liquid phase leaving only crude oil and phosphatides.

8. The method of claim 7, in which the phosphatides comprise a highly dispersible lecithin.

9. The method of claim 8, in which said lecithin is subsequently degummed from said non-aqueous liquid phase by the addition of water to hydrate the lecithin and said hydrated lecithin is thereafter centrifugally separated from said oil to obtain a highly water-dispersible lecithin.

10. The method of claim 1, including the step of subsequently degumming said phosphatides from said non-aqueous liquid phase by the addition of water to hydrate said phosphatides, and thereafter centrifugally separating the resulting hydrated phosphatides from said oil.

11. A highly water-dispersible lecithin separated from the full miscella by the method of claim 9, said lecithin containing about: 282 ppm tocopherol, 628 ppm choline chloride; and sterols in the total amount of 0.72 wt. % including 0.16% campesterol, 0.17% stigmasterol and 0.39% sitosterol.

12. In a solvent extraction method of processing oilseed containing choline chloride, employing a ternary solvent mixture including an oleophilic hydrocarbon solvent; a lower alcohol miscible with water and with said hydrocarbon solvent; and water; and one of the extracted materials is a full miscella containing crude oil and phosphatides, the ratios of said hydrocarbon solvent to said lower alcohol, and of said lower alcohol to water in said ternary solvent mixture both exceeding the ratios of the respective solvents in the ternary azeotrope formed by said ternary solvent mixture when heated to its azeotropic vapor temperature, the steps comprising:
   a. separating a non-aqueous liquid phase containing oil and phosphatides (lecithin) by subjecting said ternary solvent mixture to heat to cause the ternary solvent mixture to vaporize at its azeotropic distillation temperature until substantially all water has been removed from said ternary solvent mixture; and
   b. thereafter recovering a highly water-dispersible phosphatide (lecithin) product from said non-aqueous liquid phase, said phosphatide product having a test analysis of about 1800 ppm choline chloride.

13. The method of claim 12, in which the oilseed is soybean and the ternary solvent mixture comprises hexane, a lower alcohol, and water.

14. The method of claim 13, in which the lower alcohol is ethanol.

15. The method of claim 14, in which the solvent ratios prior to said separation exceed 7.1 parts hexane:1 part ethanol; and 4.0 parts ethanol:1 part water by adding one or more of said solvents.

16. The method of claim 15, in which the ternary solvent mixture distills at a temperature of about 56° C. at atmospheric pressure, and the distillation is continued until the temperature of the vapor phase changes from 56° C., thereby insuring substantially complete removal of water from said upper phase.

17. A highly water-dispersible lecithin separated from a ternary solvent mixture by the method of claim 12, and the further steps of heating the resulting non-aqueous liquid phase to remove substantially all remaining hexane and lower alcohol, leaving only a crude oil containing phosphatides, and thereafter separating said phosphatides from said crude oil to obtain a highly water-dispersible lecithin containing about 363 ppm tocopherol, 1800 ppm choline chloride, and sterols in the total amount of 0.54 weight percent including 0.13% campesterol, 0.13% stigmasterol and 0.28% sitosterol.

18. A blended lecithin product having good water dispersibility comprising in combination:

a. 10–30% by weight of the highly water-dispersible lecithin product of claim 17; and
b. 90–70% untreated lecithin product having less water dispersibility than said highly water-dispersible lecithin product, the resulting blended lecithin product having good water dispersibility.

19. A highly water-dispersible lecithin product obtained by the method of claim 15, including the further steps of heating the non-aqueous liquid phase to remove substantially all remaining hexane and lower alcohol, leaving only a crude oil containing said water-dispersible lecithin product, and thereafter separating said lecithin product from said crude oil, said lecithin product having a choline chloride analysis more than twice that of untreated lecithin products.

20. A highly water-dispersible lecithin product obtained by the process of claim 9, said lecithin product having a sterol content about 1 and ⅓ more than untreated lecithin product.

* * * * *